United States Patent [19]

Grendahl

[11] Patent Number: 4,787,903
[45] Date of Patent: Nov. 29, 1988

[54] INTRAOCULAR LENS

[76] Inventor: Dennis T. Grendahl, Excelsior Bay Gables, Excelsior, Minn. 55331

[21] Appl. No.: 758,331

[22] Filed: Jul. 24, 1985

[51] Int. Cl.$^4$ .............................................. A61F 2/16
[52] U.S. Cl. ...................................................... 623/6
[58] Field of Search ...................... 623/6; 350/303, 379

[56] References Cited

U.S. PATENT DOCUMENTS

| 4,010,496 | 3/1977 | Neefe ........................................ 623/6 |
| 4,373,218 | 2/1983 | Schachar ................................. 623/6 |
| 4,564,267 | 1/1986 | Nishimoto ........................... 350/379 |
| 4,601,545 | 7/1986 | Kern ........................................ 623/4 |

OTHER PUBLICATIONS

"Image Polarization Characteristics Storage in Birefringent Crystals", *Optics Communications*, pp. 297-300, May 1977, vol. 21, #2, Petrov et al.
CILCO Lens ' Style Sheet, Aug. 1983.

*Primary Examiner*—Richard J. Apley
*Assistant Examiner*—James Prizant
*Attorney, Agent, or Firm*—Hugh D. Jaeger

[57] ABSTRACT

An intraocular lens including an annular Fresnel lens for implant in the anterior chamber, the posterior chamber or in the cornea of the eye. The Fresnel lens can be made of polymethylmethacrylate (PMMA) or a high index of refraction material. The lens is an annular lens with centers of curvature of different rings receding from the axis according to the distance from the center so as to minimize spherical aberration where the only spherical surface is the central part of the lens, that central part can be plano-convex. A composite material can overlay the Fresnel elements providing a smooth entrant surface. The composite material can be a crystalline or other material which changes index of refraction when excited with electrical power or radiant energy.

7 Claims, 7 Drawing Sheets

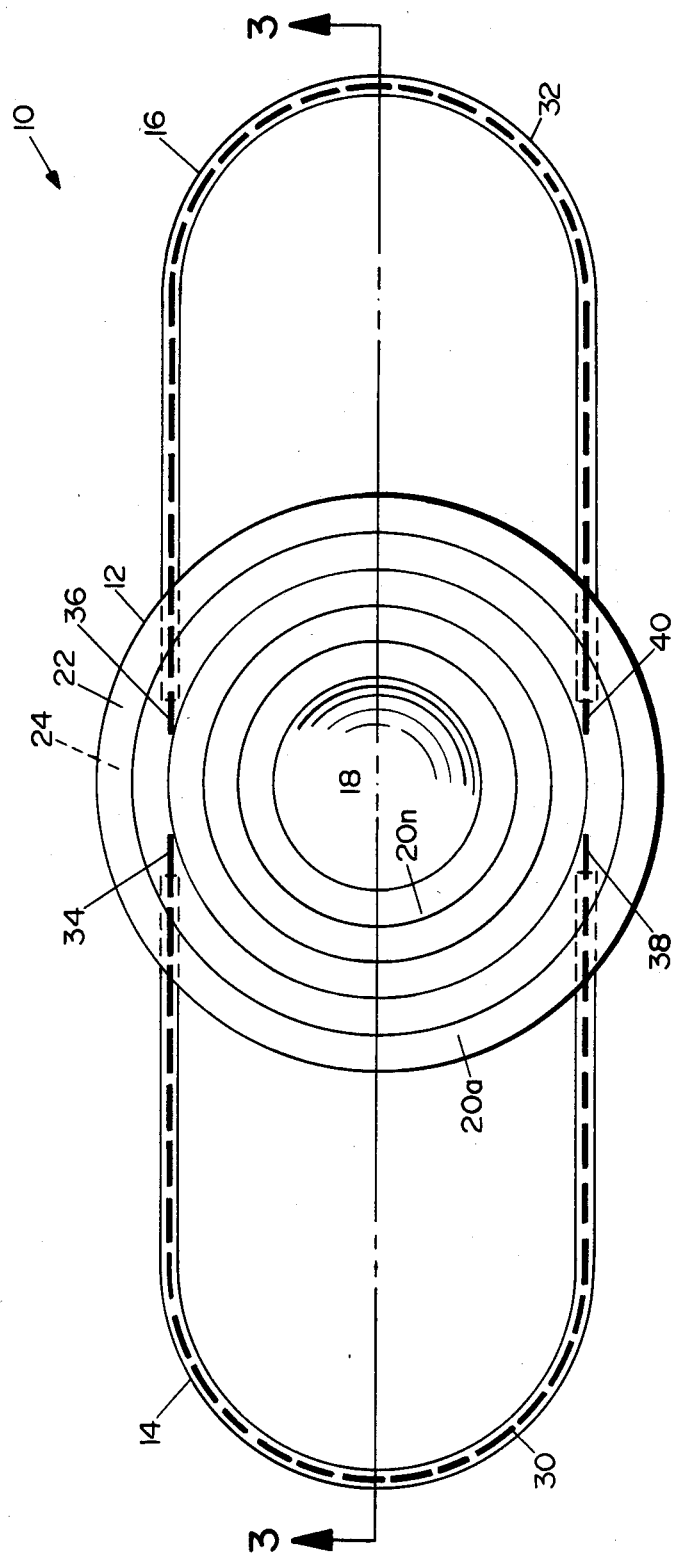
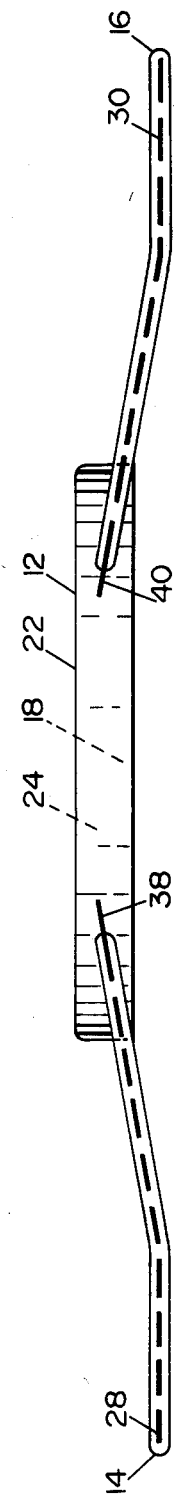

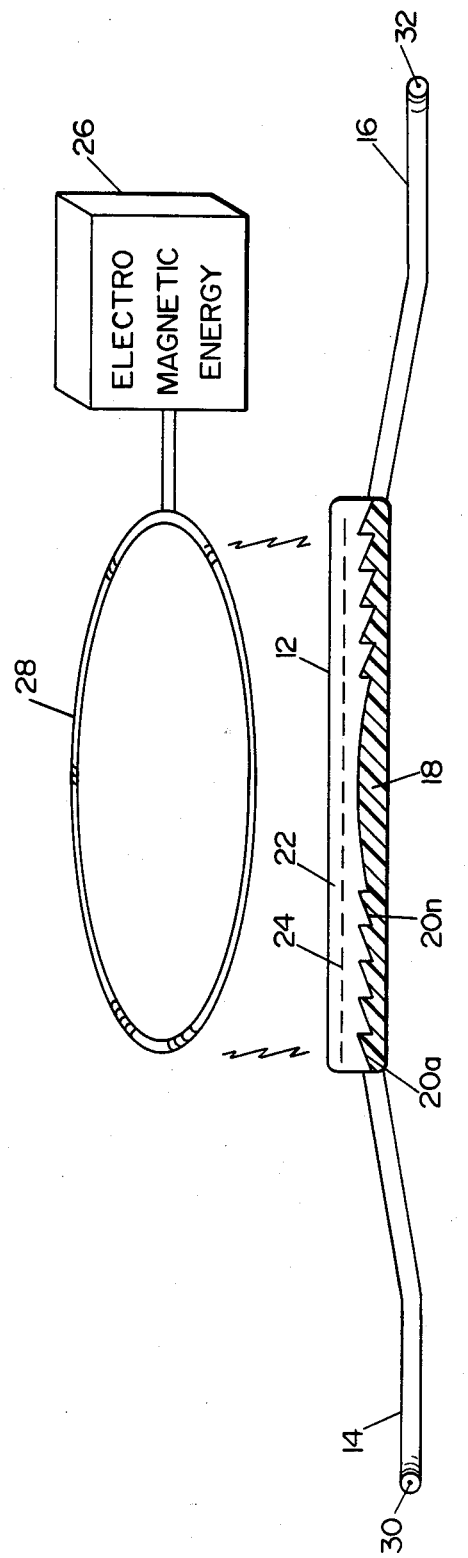

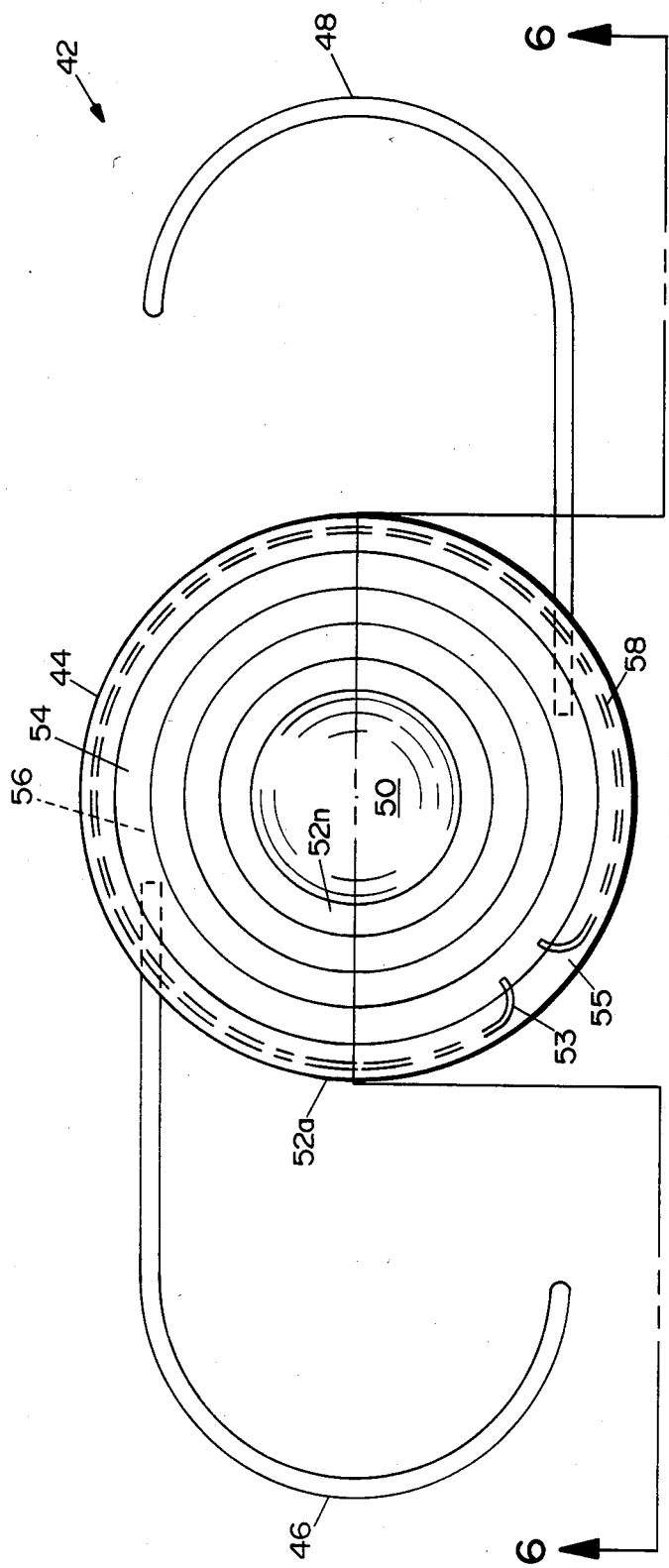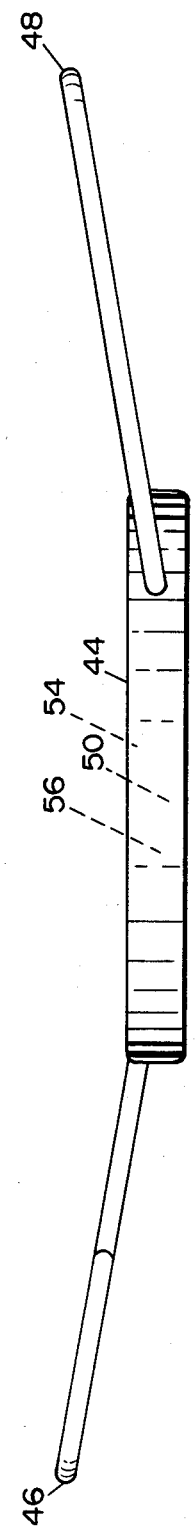

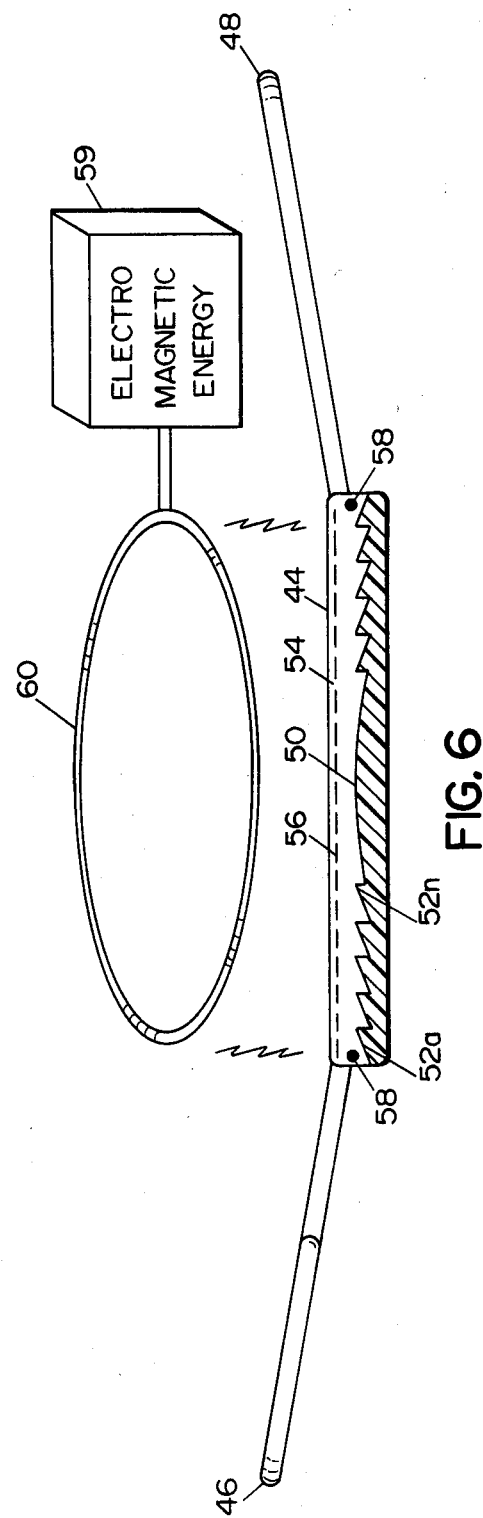

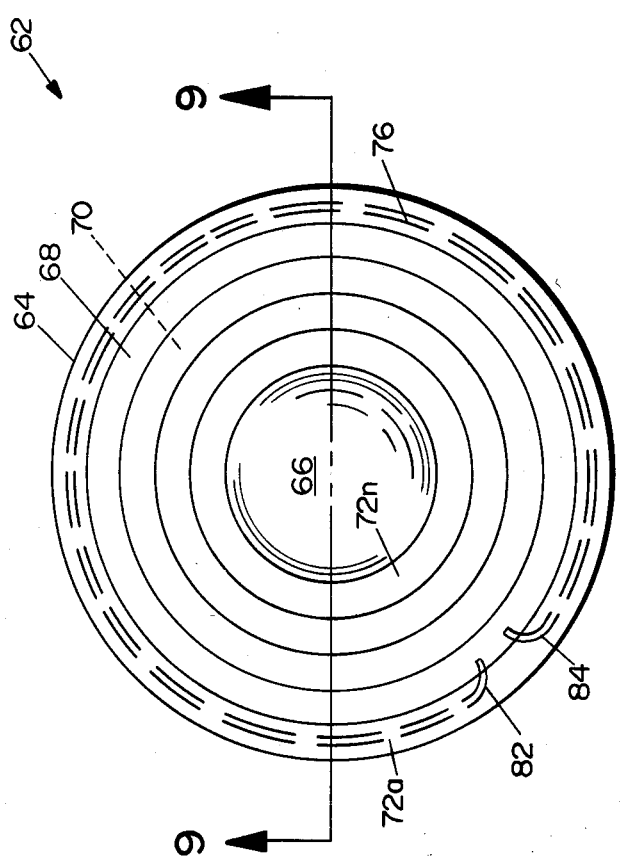
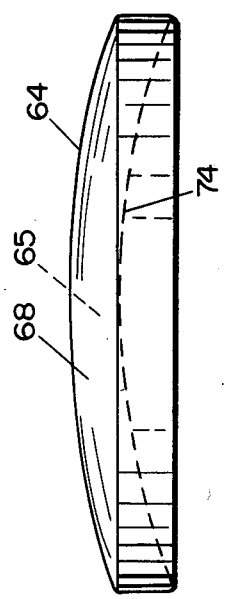
FIG. 7
FIG. 8

INTRAOCULAR LENS

BACKGROUND OF THE INVENTION

1. Field of the Invention

The present invention pertains to intraocular lenses, and intraocular lenses capable of modification after implantation in the eye, and more particularly, to an intraocular lens or corneal lens using an annular Fresnel lens.

2. Description of the Prior Art

None of the prior art lenses known to the applicant have utilized the Fresnel lens configuration. None of the prior art lenses known to applicant have utilized composite material in a lens which electroptically changes the index of refraction.

The present invention provides a composite lens with material which electroptically changes the index of refraction. Also, the composite lens can include piezo electric material in the loops to control the material. Further, the composite lens can also include a Fresnel lens structure.

SUMMARY OF THE INVENTION

The general purpose of the present invention is to provide an intraocular lens or corneal lens incorporating an annular Fresnel lens.

According to one embodiment of the present invention, there is provided an anterior chamber lens or posterior chamber lens, including loops for supporting the intraocular lens in the anterior or posterior chamber, which includes an annular Fresnel lens.

In another embodiment of the present invention, there is provided a corneal inlay, the corneal lens including an annular Fresnel lens.

Still another embodiment of the present invention includes an intraocular lens having an annular Fresnel lens and a composite overlay which has an index of refraction alterable by radiant energy or like application of electrical energy from an electromagnetic source outside of the eye. The composite overlay changes refraction due to pressure on the material by loops in contact with the capsular bag.

One significant aspect and feature of the present invention is an intraocular lens or corneal inlay which refracts, condenses, and parallels the light rays in all planes in accordance with Fresnel lens principles. The lens also focuses the image on the retina directly, or, in the case of the intracorneal inlay, focuses on the natural crystaline lens which can then still accommodate incident light to focus on the retina, or if the natural crystaline lens has been removed as in the aphacic the intracorneal inlay lens can focus directly on the retina.

Having thus described embodiments of the present invention, it is a principal object hereof to provide an intraocular lens or corneal inlay having an annular Fresnel lens.

One object of the present invention is to provide an intraocular lens with an annular Fresnel lens. The intraocular lens has loops attached for facilitating mounting in either the anterior or posterior chamber of the eye.

Another object of the present invention is to provide a corneal lens having an annular Fresnel lens.

A still further object of the present invention is to provide an intraocular lens or corneal inlay having a composite element, the index of refraction of which can be altered by the application of radiant energy or electrical energy from a power source outside the eye. In the application of an intraocular lens, pressure placed on the loops may change the index of refraction of the lens through piezo electric material composite in the loops. The composite material can be used with a Fresnel lens structure or any other lens structure such as a meniscus optic, bi-convex, plano-convex, etc.

BRIEF DESCRIPTION OF THE DRAWINGS

FIG. 1 illustrates a top view of an anterior chamber intraocular lens including an annular Fresnel lens;

FIG. 2 illustrates a side view of the lens shown in FIG. 1;

FIG. 3 illustrates a cross-sectional view of the lens shown in FIG. 1 taken along lines 3—3 of FIG. 1;

FIG. 4 illustrates a top view of a posterior chamber intraocular lens including an annular Fresnel lens;

FIG. 5 illustrates a side view of the lens shown in FIG. 4;

FIG. 6 illustrates a cross-sectional view of the lens shown in FIG. 5 taken along lines 6—6 of FIG. 4;

FIG. 7 illustrates a corneal inlay with an annular Fresnel lens;

FIG. 8 illustrates a side view of a corneal inlay with an annular Fresnel lens;

DETAILED DESCRIPTION OF THE PREFERRED EMBODIMENTS

Figure 9:
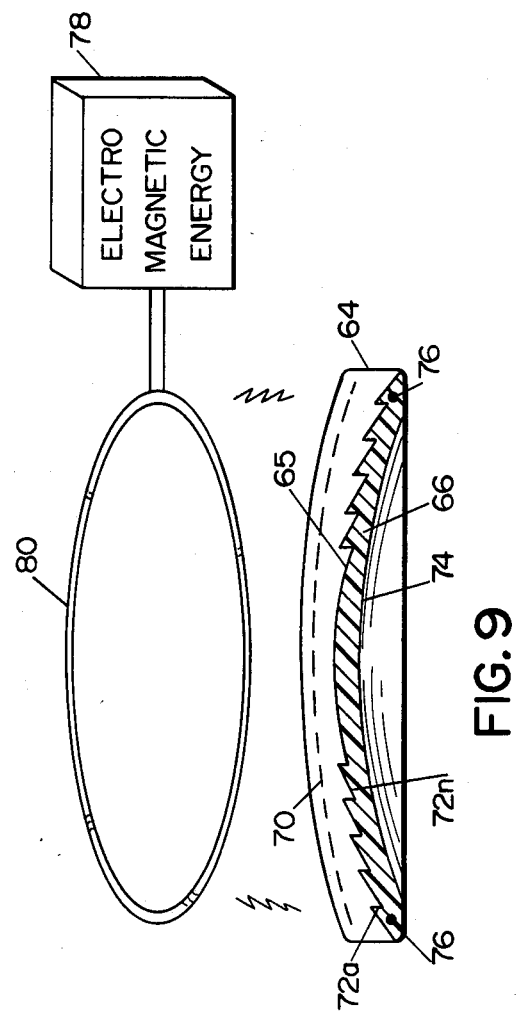
FIG. 9 illustrates a cross-sectional view of the lens shown in FIG. 7 taken along lines 9—9 of FIG. 7; and, FIG. 10 illustrates a top view of an alternative embodiment with piezo electric material.

FIG. 1 illustrates an intraocular lens 10 of the present invention, including a Fresnel annular lens optic 12 and two vaulted loops 14 and 16 secured with the lens optic 12. The loops can be any desirable shape and can be vaulted. The loops and lens optic can be made of any suitable material such as PMMA or polysulfone. The optic can be plano-convex, bi-convex, or convex-concave.

FIG. 2 illustrates a side view of the lens shown in FIG. 1. The lens optic 12 includes a Fresnel lens having a plano-convex central portion 18, as also shown in FIG. 3, and a plurality of concentric Fresnel rings 20a–20n with centers of curvature varying in accordance with the radial distance from the center of central portion 18, so as to eliminate spherical aberration. A composite overlay material 22, of clear compound, provides a smooth surface to protect the top edges of rings 20a–20n, and therefore, the eye from the sharp edges, or can also be used as a modifying system of minimizing or maximizing the index of refraction of the Fresnel or other lens of the composite. The overlay 22 is not required for operation of the lens in the eye since loops 14 and 16 position the lens optic away from the interior surfaces of the eye. The lens can be provided as a plus or minus lens.

FIG. 3 illustrates a cross-sectional view of the lens of FIG. 1 taken along lines 3—3 where all numerals correspond to those elements previously described. The overlay 22 includes a material 24 having an index of refraction which is alterable by the application of an electric field or electromagnetic radiation. This material, which can be a liquid crystal material or crystalline lattice, provides a change in the index of refraction, and therefore, also the power of the lens. The index of refraction can be variable dependent on the magnitude of the electrical field applied to the material 24 or the amount of electrical power applied to the material 24. Some materials can be switchable between more than two states, each with a different index of refraction. Other materials will provide a continuously variable index of refraction which may be stable or return to the initial value when the energy is removed. In the alternative, piezo electric material 108 and 110 can be placed in the loops 104 and 106 and connected to the composite material 112 across the optic 102. The piezo electric material generates energy when pressure is applied against the loops such as by one pressing on the eyeball forcing the loops downwardly or electrical energy is induced into the loops, thereby generating electrical energy and changing the index of refraction of the composite material of the lens of FIG. 10.

The field across material 24 is created from an external power source 26 feeding a coupling loop 28, which could be carried in an eyeglass frame, implanted about the eye socket or positioned by the individual or the Ophthalmologist. The lens carries a complementary loop or other energy pick-up device, not shown, for receiving the power. If desired, the loops 14 and 16 could be made of conductive material or carry conductive means 30 and 32 embedded therein. In either case, a connection to the material 24 would be made at the points 34, 36, 38, and 40 where the loops connect to the lens optic 12. Suitable conductors, not shown, convey the induced energy to the overlay material 24. In the event that a material is selected which changes the index of refraction only in response to a d.c. field, rectifier elements may be incorporated in the assembly to convert the a.c. to d.c. It would also be possible to utilize the induced energy to realign the molecular structure of the loop material and increase memory of the loops 14 and 16. It will be appreciated that suitable conductors, not shown, are included on the sides of material 24 or on the front and rear surfaces to allow the induced power to generate a field in the direction appropriate for alteration of the index of refraction. Such conductive elements would be so small as not to interfere with vision; or, in the alternative, a conductive material could be applied across the surface layers so thin that the light attenuation would be minimal or at least in the range acceptable for normal vision of the user.

If a material having an index of refraction which is alterable by the application of electromagnetic radiation in the visible or ultraviolet spectrum is selected, conductive loops may not be required. This embodiment would advantageously have material in the assembly which would prevent the radiation from damaging the interior of the eye.

FIG. 4 illustrates a top view of a posterior chamber Fresnel lens 42 including a lens optic 44 and two loops 46 and 48 extending therefrom. The Fresnel lens optic 44 includes a plano-convex central portion 50, as also shown in FIG. 6, positioned centrally within a plurality of Fresnel rings 52a–52n. The centers of curvature of Fresnel rings 52a–52n vary according to the radial distance from the center of central portion 50 to essentially eliminate spherical aberration and govern refraction. The loops 46 and 48 can be made of PMMA or other suitable material and can be angled at any desired value.

A composite overlay 54 of clear material provides protection for the top edges of the Fresnel rings. The material used for composite overlay 54 should provide a smooth surface and may include a liquid crystal or crystalline lattice material 56 which has an index of refraction alterable by the application of an electric field or other forms of radiation. If the material having an index of refraction alterable through the application of electrical power is selected, a pick-up loop 58 may be embedded in the lens optic 44 and connected to the material 56 at points 53 and 55. In the event that a d.c. field is required, rectifier diodes could be inserted in the circuit with loop 58 to provide a d.c. voltage to the material 56 through suitable conductors or conductive surface as described with reference to the previously discussed embodiments of FIGS. 1, 2, and 3.

FIG. 5 illustrates a side view of the posterior chamber lens 42 of FIG. 4 where all numerals correspond to those elements previously described.

FIG. 6 illustrates a cross-sectional view of the lens taken along lines 6—6 of FIG. 4 where all numerals correspond to those elements previously described. The lens is provided with a composite overlay material 54 and liquid crystal or crystalline lattice material 56 or like material having an alterable index of refraction. In the event that a material is selected which is alterable through the application of electromagnetic energy, an electromagnetic source 59 coupled to a loop 60 can be used to change the index of refraction in the ways previously described.

FIG. 7 illustrates a top view of a Fresnel intracorneal lens 62 including a lens optic 64 with concave-convex central portion 66 and a Fresnel lens portion of Fresnel rings 72a–72n including a composite overlay 68. In contrast to the embodiments earlier described, the anterior surface of concentric Fresnel rings 72a–72n conforms to the concave curvature 74, as illustrated in FIG. 9, which is a cross-sectional side view of the lens of FIG. 7. An induction loop 76 positioned within the lower edge of optic 64 connects to the crystalline material as points 82 and 84.

FIG. 8 illustrates a side view of a corneal inlay with an annular Fresnel lens where all numerals correspond to those elements previously described.

FIG. 9 illustrates a cross-sectional view of the lens taken along lines 9—9 of FIG. 7 where all numerals correspond to those elements previously described. The lens is provided with a composite overlay 64 having a material 70 which has an index of refraction alterable through the application of electromagnetic energy. Such energy can be obtained from a source 78 coupled to a loop 80.

Figure 10:
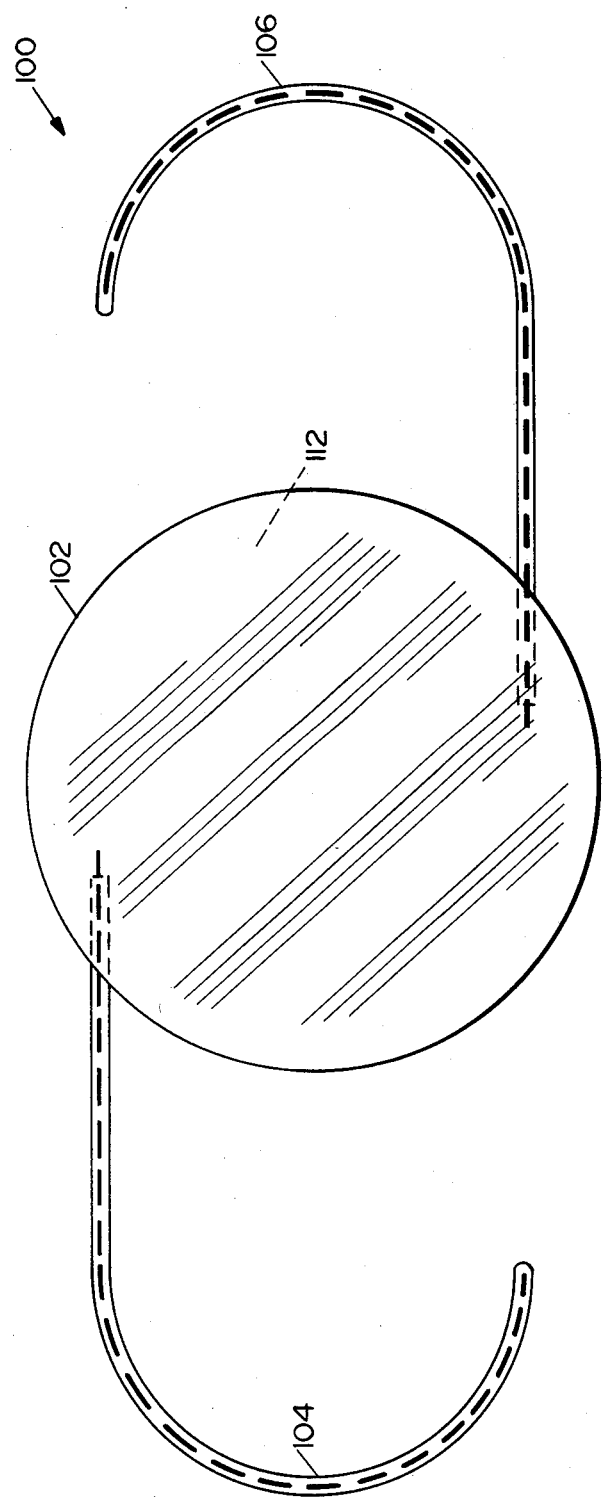

FIG. 10 illustrates an alternative embodiment of the present invention including a lens 100 utilizing piezo electric material 108 and 110 in the loops 104 and 106. The loops are connected to the optic 102 by available processes. The piezo electric material connects to the composite material 112. The composite material is excited when energy is generated by the piezo electric loops. The energy can either be generated by pressure against the loops causing the piezo electric material to generate voltage across the composite material, or in the alternative, electrical energy can be induced into the piezo electric material and the loops causing energy to be communicated to the composite material 112.

Figure 11:
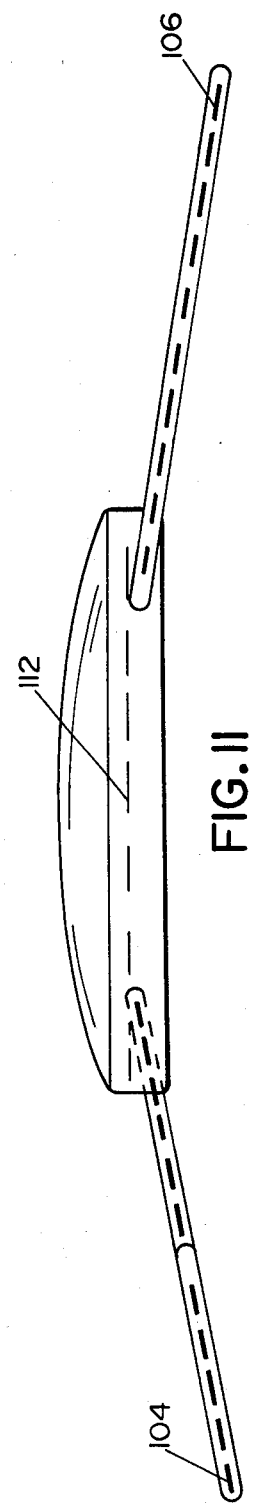
FIG. 11 illustrates a side view of FIG. 10.

FIG. 11 illustrates a side view of FIG. 10 where all numerals correspond to those elements previously described.

It is claimed:

1. An intraocular lens comprising:

a. a lens optic including an anterior surface and a plano posterior surface, said anterior surface including a Fresnel lens portion;
b. said lens inclucding a composite overlay material over the front surface of said Fresnel lens portion wherein said composite overlay material includes a material having an alternate bulk optical index of refraction; and
c. a plurality of haptic loops which support the lens in the eye, extending outwardly from said lens optic, said loops including conducive portions connected to said alterable material for coupling electrical power applied from a source external to the eye.

2. A lens of claim 1 wherein said loops are closed and vaulted for supporting said lens in an anterior chamber of an eye.

3. A lens of claim 1 wherein said loops are open for supporting said lens in a posterior surface of an eye.

4. A lens of claim 3 wherein said loops are vaulted.

5. A lens of claim 1 wherein said index of refraction is alterable in accordance with the magnitude of an electrical field applied across said material.

6. A lens of claim 1 wherein said index of refraction is alterable in accordance with the amount of electromagnetic radiation applied to said material.

7. A lens of claim 1 comprising a source of piezo electricity internal to said loops for powering said alterable material.

* * * * *